United States Patent [19]

Harjunmaa

[11] Patent Number: 5,099,123
[45] Date of Patent: Mar. 24, 1992

[54] METHOD FOR DETERMINING BY ABSORPTION OF RADIATIONS THE CONCENTRATION OF SUBSTANCES IN ABSORBING AND TURBID MATRICES

[75] Inventor: Hannu Harjunmaa, Vessy, Switzerland

[73] Assignee: Biosensors Technology, Inc., Worcester, Mass.

[21] Appl. No.: 527,514

[22] Filed: May 23, 1990

[30] Foreign Application Priority Data

May 23, 1990 [EP] European Pat. Off. ...... 89 81 0382.5

[51] Int. Cl.$^5$ ............................................. G01J 1/16
[52] U.S. Cl. .................................. 250/345; 250/339; 250/343; 356/39; 128/633
[58] Field of Search ........ 250/339, 341, 343, 252.1 A, 250/345; 356/41, 435, 39; 128/633, 664

[56] References Cited

U.S. PATENT DOCUMENTS

| | | | |
|---|---|---|---|
| 1,758,088 | 5/1930 | Schmick . | |
| 2,721,942 | 10/1955 | Friel et al. | 250/43.5 |
| 3,463,142 | 8/1969 | Harte | 128/633 |
| 3,489,906 | 1/1970 | Beer | 356/435 |
| 3,638,640 | 2/1972 | Shaw | 356/41 |
| 3,926,527 | 12/1975 | Pembrook et al. | 356/246 |
| 3,958,560 | 5/1976 | March | 356/39 |
| 3,963,019 | 6/1976 | Quandt | 356/39 |
| 4,029,085 | 6/1977 | DeWitt et al. | 128/2 R |
| 4,033,330 | 7/1977 | Willis et al. | 356/39 |
| 4,169,676 | 10/1979 | Kaiser | 128/633 |
| 4,266,554 | 5/1981 | Hamaguri | 128/633 |
| 4,267,844 | 5/1981 | Yamanishi | 128/633 |
| 4,306,877 | 12/1981 | Lübbers | 23/230 R |
| 4,321,930 | 3/1982 | Jöbsis et al. | 128/633 |
| 4,380,240 | 4/1983 | Jöbsis et al. | 128/633 |
| 4,398,541 | 8/1983 | Pugliese | 128/665 |
| 4,427,889 | 1/1984 | Müller | 250/339 |
| 4,485,820 | 12/1984 | Flower | 128/633 |
| 4,513,751 | 4/1985 | Abe et al. | 128/2 R |
| 4,570,638 | 2/1986 | Stoddart et al. | 128/665 |
| 4,586,513 | 5/1986 | Hamaguri | 128/633 |
| 4,603,700 | 8/1986 | Nichols et al. | 128/633 |
| 4,621,643 | 11/1986 | New, Jr. et al. | 128/633 |
| 4,653,498 | 3/1987 | New, Jr. et al. | 128/633 |
| 4,655,225 | 4/1987 | Dähne et al. | 128/633 |
| 4,704,029 | 11/1987 | Van Heuvelan | 356/39 |
| 4,725,147 | 2/1988 | Stoddart | 356/433 |
| 4,750,496 | 6/1988 | Reinhart et al. | 128/635 |
| 4,759,369 | 7/1988 | Taylor | 128/633 |
| 4,768,516 | 9/1988 | Stoddart et al. | 128/665 |
| 4,796,636 | 1/1989 | Branstetter et al. | 128/633 |
| 4,805,623 | 2/1989 | Jöbsis | 128/633 |
| 4,817,623 | 4/1989 | Stoddart et al. | 128/665 |
| 4,832,484 | 5/1989 | Aoyagi et al. | 356/41 |
| 4,882,492 | 11/1989 | Schlager | 250/346 |
| 5,028,787 | 7/1991 | Rosenthal et al. | 250/341 |

FOREIGN PATENT DOCUMENTS

PCT/US90/-
00394   1/1990   PCT Int'l Appl. .
0160768  4/1984   Switzerland .

OTHER PUBLICATIONS

"Blood Glucose Sensors: An Overview"]by R. A. Peura and Y. Mendelson-1984, pp. 63-68, IEEE/NSF Symposium on Biosensors.

*Primary Examiner*—Carolyn E. Fields
*Assistant Examiner*—James E. Beyer
*Attorney, Agent, or Firm*—Hamilton, Brook, Smith & Reynolds

[57] ABSTRACT

A method and apparatus for non-invasively testing analytical substances in turbid matrices i.e. body fluids and tissues. In this method a sample is irradiated with a beam of electromagnetic energy at two alternating wavelenths, $\lambda_1$ and $\lambda_2$, at which the absorption by the background is the same but at one of which the radiation is absorbed by the analyte and at the other it is not. The apparatus comprises means which enable to control the input energy at $\lambda_1$ and $\lambda_2$ so that at the output from the sample the electric signals issuing after detection cancel in the absence of the analyte in the sample. When analyte is present cancellation no longer occurs and a signal proportional to the analyte concentration in the sample is produced. The apparatus is also designed for shifting the response back to zero when a calibrating known concentration of analyte is used as standard, thus providing a controllable zeroing base line.

11 Claims, 1 Drawing Sheet

METHOD FOR DETERMINING BY ABSORPTION OF RADIATIONS THE CONCENTRATION OF SUBSTANCES IN ABSORBING AND TURBID MATRICES

BACKGROUND OF THE INVENTION

1. Field of the Invention

This invention relates to the non-invasive measurement of the concentration of substances that absorb electromagnetic radiation, such as light or infrared radiation, in absorbing and turbid matrices such as human or animal body tissue using a probe beam of electromagnetic radiation. The method and apparatus used to make the measurement according to this invention are fully described in the annexed claims and in the following description accompanied by figures.

The invention is described as applied to the special case of glucose measurement in human tissue using near-infrared radiation. This should in no way detract from the general applicability of the invention to measure the concentration of any species that absorbs electromagnetic radiation, especially in strongly absorbing and turbid matrices.

2. Description of the Prior Art

The infrared measurement methods known in the art are not well adapted to the problem of quantifying an analyte dissolved in a strongly absorbing solvent. The known methods include separate or directly alternating measurements using radiations at a "glucose" wavelength and at a "reference" wavelength, where glucose does not absorb, as well as differential wavelength modulation about a glucose absorption band (C. Dähne, D Gross, European Patent 0 160 768 and references therein). In the known methods, the signal is easily lost into the variable and strong background presented by the water in the tissues and in the capillary blood flow. The reference concentration range of glucose in blood is 2.8–5.5 mmol/l.

SUMMARY OF THE INVENTION

The essential difference between the method proposed here and those known in the art is that, in contrast to the known methods, the method of this invention forms the difference of the signals obtained at an analyte wavelength $\lambda_1$ the analyte, in this case glucose, absorbs), and a reference wavelength $\lambda_2$ (where the analyte essentially does not absorb) directly at the optical level (i.e. by optical means), instead of comparing electronically the two signals at the analog or digital level (i.e. by electronic circuitry means). The two wavelengths $\lambda_1$ and $\lambda_2$ are selected so that the radiation has exactly the same degree of matrix absorption at these wavelengths.

In the method of this invention, the measurement is made by combining into a single beam alternate pulses defined hereafter as "half-periods" of near IR radiation at the two wavelengths, directing the beam against the sample, thus providing a response beam to be detected by a single detector. With no analyte present, the $\lambda_1$ and $\lambda_2$ half-periods in the response beam cancel at the detector. When the sample contains glucose, the amplitude of the alternating-current (AC) signal given by the detector is representative of the glucose concentration or of the difference with a preset reference concentration. The measurement geometry may be either direct transmission, transflection or attenuated total reflection. The measurement system automatically normalizes its sensitivity at the two wavelengths so as to give a zero AC output signal from the matrix with zero glucose concentration. Alternatively if desired, any known non-zero glucose concentration may be used to establish a zero-point, thus allowing to establish a personalized calibration without the need to reduce the glucose concentration to zero in the test subject. This scheme has the following advantages:

Because the zero-point AC signal is substantially zero, high sensitivity lock-in techniques can be used to extract the glucose signal. The absorption of water does not interfere, since it is automatically cancelled out. The system, so as to say, locks itself on the background signal.

With a proper choice of parameters, the output signal is almost independent of the path length over a limited, but useful, range. This also makes the system less sensitive to background fluctuations and scattering and partly cancels the displacement effect (solute displaces solvent).

The system is conceptually simple. It gives a direct-reading signal related in a simple way to the glucose concentration. No elaborate spectrum correlation techniques are needed.

The measuring system must have the following special properties:

The intrinsic extinction (absorption+scattering) coefficient of the tissue must be exactly the same at the reference and glucose wavelengths. "Exactly" here means to an accuracy equivalent to the sensitivity desired, i.e. to the change in the total extinction coefficient produced by the desired minimum detectable amount of glucose.

DETAILED DESCRIPTION OF THE INVENTION

Figure 2:
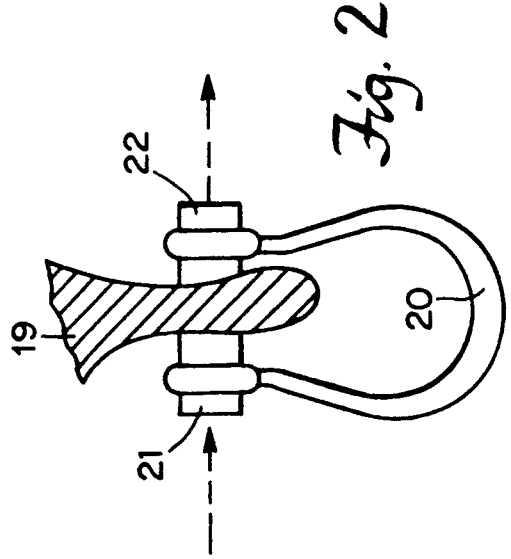
FIG. 2 illustrates schematically a probe to be used in accordance with the present invention.

The principles governing the method of the present invention are briefly outlined below with the assumption that the Beer-Lambert law, $P = P_o e^{-kx}$ is valid.

In the above relation, $P_o$ is the power of the incident collimated beam falling on the sample, k is the absorption coefficient (usually in 1/cm) and x is the length (in cm) of the sample in which interaction occurs. To simplify the equations, only essential quantities are retained and the signal is considered radiative only; scattering can be included in k, and, if its contribution is desired explicitly, it is a straightforward operation to replace k by the sum of absorption and scattering effects, whereby scattering only can be ascertained by difference.

In view of the above, the powers collected at wavelengths $\lambda_1$ and $\lambda_2$ are $P_{\lambda 1} = P_o e^{-k_1 x}$ and $P_{\lambda 2} = P_o e^{-k_2 x}$, respectively.

Since provision is made that the absorption of the background is the same at $\lambda_1$ and $\lambda_2$, the difference $$S = \Delta P = P_{\lambda 1} - P_{\lambda 2} = 0$$

When glucose is present, it absorbs at one of the wavelengths but not at the other, which means that for the first wavelength, say $\lambda_1$, the absorption coefficient has changed by, say, $\Delta k$. Hence now, $$S \neq 0 = P_0 [e^{-(k-\Delta k)x} - e^{-kx}] \text{ or}$$
$$= P_0 e^{-kx}[e^{\Delta kx} - 1]$$

Now for $\Delta k$ small i.e. <0.1, the known approximation $e^{\Delta kx} = 1 + \Delta kx$ holds; so $S = P_0\Delta kx \, e^{-kx}$, i.e. the signal is proportional to $\Delta k$, that is, to the analyte concentration.

With respect to the relation $$S = P_0\Delta kx \exp(-kx),$$

it should be noted that the function $$x \exp(-kx)$$

has interesting properties. A calculation of the relative derivative of the signal with respect to path length gives $$\frac{dS/S}{dx/x} = 1 - kx.$$

The derivative is zero when $$kx = 1, \text{ i.e. } x = \frac{1}{k}$$

At this point, the signal has a maximum and is substantially insensitive to small changes in path length (or, equivalently, to the water concentration in the tissue). The optimal path length (in cm) is simply the inverse of the common extinction coefficient. The maximum is fairly broad, and, as the second derivative is equal to $-k$, the maximum broadens with a decreasing common absorption coefficient. Hence the relative insensitivity to path length changes has the effect of increasing the sensitivity of detection, as compared with a conventional system, despite the longer path. The scattered rays that reach the detector will travel in the sample. In a conventional measurement system, the contribution of scattered energy to the signal diminishes rapidly with increasing path length. In the system of this invention, even rays that have been scattered far from the main beam contribute to the AC signal despite the attenuated DC level. In a transflection geometry, the system of this invention favors the measurement depth that corresponds to the optimal path length because of the maximum in the path length signal function.

The DC level of the radiative signal is attenuated by the factor e at the optimal path length. The optimal path length always gives an absorbance of 0.434 absorbance units (base 10) at both wavelengths.

If there is some analyte absorption at the reference wavelength, the signal diminishes in proportion to the difference of the analyte absorptions at the analyte wavelength and the reference wavelength.

In order to account correctly for scattering, the wavelength choice must be made on the basis of the sum spectrum of absorption and scattering in the tissue (that is, extinction spectrum), with due consideration to the measuring geometry, which affects the relative importance of scattering.

Table 1 below indicates a few wavelengths, (taken from EP 0 160 768) at which glucose absorbs which can be used to practice the invention in combination with the background absorption values on the same line of the Table. Water absorption coefficients at the indicated wavelengths are also in the Table.

TABLE 1

| Glucose absorption $\mu m$ | Background absorption $\mu m$ | $kH_2O$ 1/cm |
|---|---|---|
| 1.57 | 1.75 (gl)*, 1.38 (st)* | 9 |
| 1.77 | 1.55 (gl), 1.39 (st) | 7 |
| 2.10 | 2.29 (gl), 1.87 (st), 1.46 (pk)* | 30 |
| 2.17 | 1.86 (st), 1.49 (st), 1.41 (st) | 25 |
| 2.27 | 2.15 (gl), 1.86 (st), 1.48 (st), 1.40 (st) | 30 |

*st = steep; pk = peaking; gl = glucose absorption.

For fine tuning the wavelengths, one keeps a member of the pair constant while the other is adjusted. Preferably, the glucose wavelength is kept constant in order to have a constant sensitivity for glucose. The reference wavelength is preferably situated on a moderate or shallow slope of the water absorption spectrum: with a steep slope, accurate control is more difficult. In table 1, some reference wavelengths have a steep slope; others are shallow (pk); some references include glucose absorption.

The following example illustrates the invention with reference to the annexed drawings.

Because of the strength of glucose absorption at 2.1 $\mu m$, the present embodiment has been devised for the wavelength pair 2.10/1.46 $\mu m$. This wavelengths selection is only one example, no other wavelength pairs being excluded from the scope of this invention.

Further, this invention can be carried out using many other embodiments not specifically exemplified here but which should not be excluded from protection.

Figure 1:
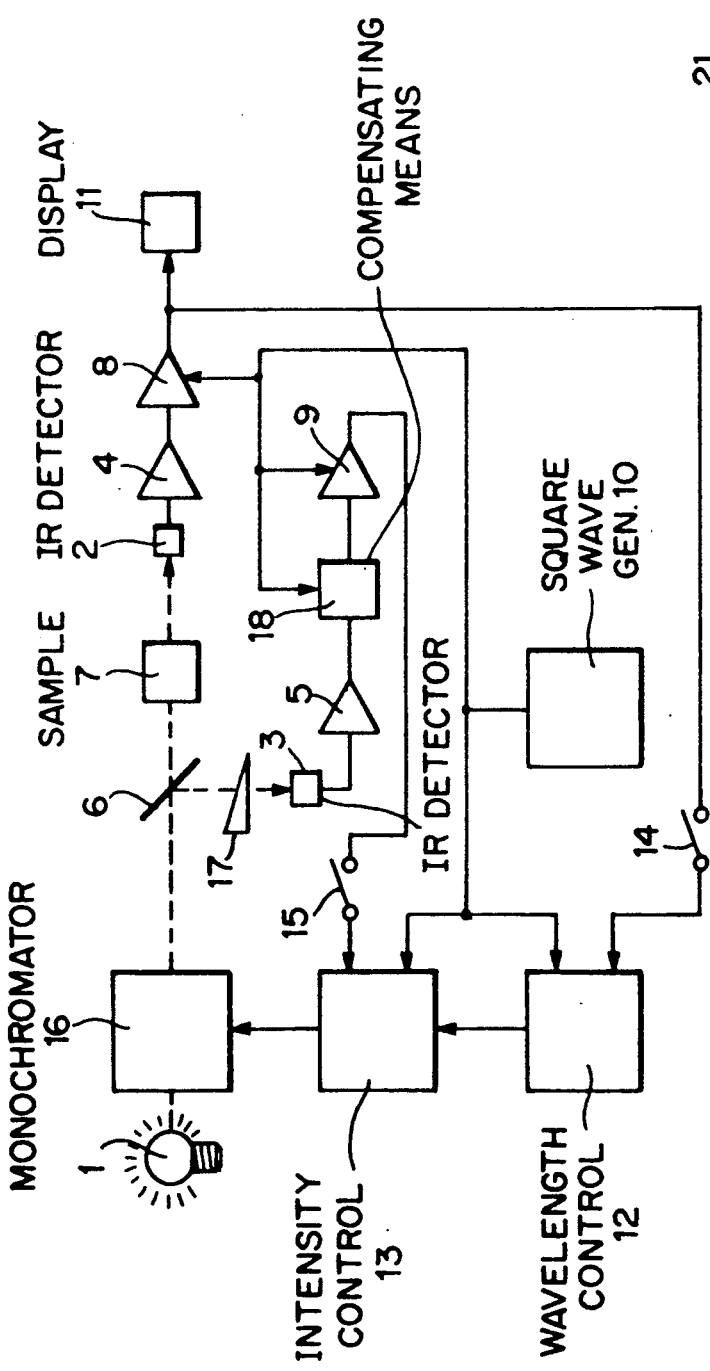
FIG. 1 is a block diagram of the components used in a device for carrying out the method of the invention.

Referring to FIG. 1, a light source (1) is near IR source for generating a beam of electromagnetic radiation. Its intensity at these wavelengths is good, and the decreasing spectral intensity is partly compensated by the increasing spectral sensitivity of photon detectors. Other light sources, such as lasers, are obviously also applicable, provided that the required wavelengths are available and that at least one of them is tunable. The beam generated is fed to a monochromator (16) where the selection of wavelengths $\lambda_1$ and $\lambda_2$ is effected.

The system uses two photoconductive PbS infrared detectors (2, 3) operating at room temperature. Their spectral sensivity peaks at about 2.2 to 2.5 micrometers. The PbS detectors are operated in the classical bolometer circuit, AC-coupled to preamplifiers (4, 5). One of the detectors (2) is used in the sample channel, and one (3) in a reference channel. Obviously, any other detector sensitive in the relevant wavelength range could be used, with the appropriate coupling and amplifying method.

The reference channel beam is split from the main beam using a spectrally neutral beam splitter (6) situated before the sample (7). The sample channel includes collimating means, i.e., lenses or mirrors to direct the sample channel beam into the sample and from the sample to the sample channel detector.

The outputs of the PbS detectors are measured using lock-in amplifiers (8, 9) that use the signal produced by a square wave generator (10) as their reference signal. The output of each lock-in is thus a rectified direct-current signal proportional to the alternating-current signal produced by the corresponding detector. The output of lock-in (8) in the sample channel is fed to a display device (11). It is important to preserve the sign (phase)

of the AC signal, because these signals are used for closed-loop control. For this reason, conventional rectification where the phase is lost cannot be used. The present circuitry takes care of this phase selection requirement.

The operation of the system is governed by the square wave generator (10). Its output determines which one of the two wavelengths and which one of the two corresponding intensity levels is to be used. The wavelength control (12) changes the wavelength between the two values and fine-tunes one of the wavelengths according to the output of lock-in (8): as long as that output is non-zero, the wavelength is changed to decrease the output, provided that the control is not locked. The intensity control (13) changes the intensity of the beam between the two values and fine-tunes one of the intensities according to the output of the lock-in (9): as long as that output is non-zero, the intensity is changed to decrease the output, provided that the control is not locked.

The wavelength control can be locked to keep the wave-lengths unchanged by opening the switch (14). The intensity control can be locked to keep the intensities unchanged by opening the switch (15).

As the monochromator, the system uses an acousto-optic tunable filter (AOTF) (16), which permits alternating the two wavelengths in rapid succession and at the same time controlling their relative intensity without any moving parts. The wavelength and intensity control signals need one connector cable only to reach the AOTF, since it is the frequency of the signal that controls the wavelength, and the intensity is controlled by the amplitude of the signal. It is obviously also possible to use other methods to select the two wavelengths needed, for instance, dividing the beam in two parts and using chopping each beam in antiphase relationship, this being done mechanically or electro-optically, using for instance a liquid crystal, and recombining the beams after monochromatization. The intensity regulation, however, would be more complicated in that case.

The reference channel has optical (17) and electrical (18) compensating means that are used to change the zero-point of the signal. Compensation is necessary to cancel the differences in the apparent relative intensity of the two wavelength channels that result from the unbalanced splitting effect of the beam-splitter and by the differences in the spectral sensitivity of the detectors. The compensating means are adjusted before measurement with the wavelength control locked (both wavelengths fixed) to give zero signal in the sample channel in the absence of the sample. During the adjustment, the reference signal servoes itself to zero by the intensity fine-tuning circuit. This establishes the basic equisensitivity of the channels at the wavelengths initially selected. This adjustment is independent of the sample, and normally needs to be done only once, unless there is a large change in the reference wavelength. Optical compensating means (17) may include wedge-pattern selective absorbers, tilted dichroic mirrors and the like. Electrical compensating means (18) include a summing amplifier and, possibly, other similar circuits. The sample (7) may constitute part of the body of a patient where glucose concentration must be measured.

The reference wavelength selected for measurement depends on the calibration of the subject to be tested. The calibration is performed at a well defined and easily available test site, such as the earlobe or the skin between fingers (19) (see FIG. 2), the glucose concentration in blood being known. This glucose in blood concentration should preferably be low. During the calibration, the sample channel and reference channel signals are zeroed iteratively. The iteration is begun with the sample signal (output of lock-in (8)), which is zeroed by varying the reference wavelength (intensity control locked), then the reference signal (output of lock-in (9)) is zeroed by varying the relative intensity of the two wavelength parts (wavelength control locked) and so on, until there is no more change in wavelength or relative intensity.

The exact reference wavelength obtained is noted and kept on record for that particular patient. The known glucose concentration, also kept on record, is set to correspond to zero signal, and the sensitivity of the signal to glucose concentration, known on the basis of previous tests and substantially constant, is used to establish the complete response function of the system.

For the actual measurement, the wavelength control is locked, the sample is introduced into the sample channel, and the output of the sample lock-in (8) is read. The reading is proportional to the difference between the actual concentration and the calibration concentration, and the concentration is obtained using the previously established response line. Note that the difference can be either positive or negative.

During the measurement, the reference channel is used to adjust the relative intensities of the two wavelength parts of the beam to produce a zero AC signal in the reference detector (3), thus cancelling possible instabilities of instrumental origin.

In an alternative embodiment of the invention, the signal obtained from the calibrator sample during calibration is not zeroed, but is set to correspond directly to the known concentration, applying a conversion factor obtained from sensitivity measurements. In this embodiment, the final reading obtained from an arbitrary sample indicates directly the glucose concentration; one only needs to apply the conversion factor inversely.

The measurement must always be done exactly at the same test site for a particular patient in order to preserve the validity of the calibration. To that effect, an optical device, interfacing with the basic optical system, may be semi-permanently attached to the test subject at a suitable text site. This is depicted schematically in FIG. 2. The optical device may, for instance, take the appearance of an earring (20), having an input element (21) on one side of the earlobe (19) and an output element (22) on the other side of the earlobe, both transparent at the measurement wavelengths. The element 20 has the property of maintaining the probe at a fixed position on the earlobe.

The following test report illustrates the performance of the device of the invention.

TEST REPORT

A series of serum samples having different glucose concentrations were measured using the apparatus disclosed in reference to FIG. 1. The sample (7) was a glass cuvette with a light path length of 1 mm. The results are presented below in table form. The different glucose concentrations were obtained from a Merz & Dade normal serum by successive additions of glucose in dry form.

| Glucose concentration mmol/l | Signal millivolts |
| --- | --- |
| 10.75 | 26 |
| 17.42 | 38 |
| 24.08 | 59 |
| 30.75 | 70 |

It can be seen that a straightforward relationship exists between the sample glucose and the readings. It was possible to extrapolate the results in applying the technique to measure glucose non-invasively in body tissues.

I claim:

1. A method for determining and measuring in a sample matrix the concentration of an analyte which absorbs substantially monochromatic electromagnetic radiations of wavelength $\lambda_1$, this analyte being dissolved or dispersed in the sample matrix, this method comprising the steps of:
   a) selecting another electromagnetic radiation of wavelength $\lambda_2$ at which the analyte does not substantially absorb, the absorption coefficient of the matrix background being substantially the same at $\lambda_2$ and at $\lambda_1$;
   b) by means of a source, generating a probing beam with alternant intensity controllable half-periods at $\lambda_1$ and $\lambda_2$, and splitting this beam with beam-splitter means into a reference split beam and a probe beam to be applied to the sample matrix, interaction of this probe beam and the sample matrix resulting into a response beam representative of the absorption of the probe beam by the sample matrix;
   c) detecting said response beam by a first detector sensitive to both $\lambda_1$ and $\lambda_2$ thus providing a detected AC test signal and detecting the split beam with a reference detector thus providing a comparison signal;
   d) optically controlling the intensity ratio of $\lambda_1$ and $\lambda_2$ half-periods using the signal from the second detector to calibrate the probing beam so that the AC signal of the first detector is essentially zero in the absence of the analyte in the sample matrix;
   e) shining the calibrated probing beam to a sample matrix containing a concentration of the analyte, whereby a nonzero signal arises at the first detector, the value of this detected signal being representative of said desired determination and measurement.

2. Method according to claim 1, in which the probe beam is applied to a calibrator representative of the matrix and having an essentially zero concentration of the analyte, and for effecting step d) one of the two different wavelengths is tuned to obtain an essentially zero signal from the first detector.

3. Method according to claim 1, in which the probe beam is applied to a calibrator representative of the matrix and having a known concentration of the analyte and instead of effecting step d) one of the two different wavelengths is tuned to obtain a signal value related to the known concentration from the first detector.

4. Apparatus to determine an unknown concentration of an analyte that absorbs electromagnetic radiation and is dissolved or dispersed in a sample matrix, comprising:
   a) generating means for generating an uninterrupted probe beam of the radiation which contains, alternating in time at a suitable alternating frequency, half-periods of two different and substantially monochromatic wavelengths $\lambda_1$ and $\lambda_2$ such that, at the two wavelengths, the extinction caused by the combined effects of absorption and scattering in the matrix is equal, but the absorption produced by the analyte is different;
   b) splitting means for splitting this beam into a reference beam to provide a reference signal to be detected by a reference detector and a test beam to provide an AC test signal to be detected by a test detector;
   c) optical means for transmitting the test beam into a sample of the sample matrix;
   d) collecting means for collecting a response of the test beam after it has traversed the sample, said collecting means comprising the test detector which is sensitive to both said wavelengths and providing in response said AC test signal;
   e) amplification means to amplify and rectify this AC test signal from the test detector at the wavelength-alternating frequency, to produce a DC test signal;
   f) compensating means for optically controlling the intensity ratio of the $\lambda_1$ and $\lambda_2$ half-periods so that the DC signal from the amplification means will be essentially zero when there is no analyte in the sample;
   g) control means for maintaining constant the intensity ratio of the two different wavelength half-periods of the probe beam when analyte is present in the sample using the reference signal from the reference detector; and
   h) display means for displaying the DC signal from the amplification means.

5. Apparatus according to claim 4, having optical compensating means to change the intensity relation of the two different wavelength half-periods of the probe beam apparent to the reference detector.

6. Apparatus according to claim 4, having electrical compensating means to change the sensitivity relation of the reference detector to the two different wavelength parts of the uninterrupted probe beam.

7. Apparatus according to claim 4, in which the analyte is glucose to be measured in human or animal body tissue, the two different wavelengths being selected from the interval 1–2.5 μm.

8. Apparatus according to claim 4, in which the means of generating the radiation beam include an acousto-optic device.

9. Apparatus according to claim 4, in which the means of transmitting the test beam into the sample and the means of collecting the response of the test beam after it has traversed the sample include one or more optical elements that are attached to the sample and can be repeatedly taken out of and returned to the optical circuit of the measurement system together with the sample to allow the measurement to be repeated a multitude of times at constant geometrical relationship to the sample.

10. Method according to claim 1, in which the distance of penetration of the probe beam into the sample where interaction occurs is, expressed in cm, the inverse of the absorption coefficient of the background medium.

11. Apparatus to determine an unknown concentration of an analyte that absorbs electromagnetic radiation and is dissolved or dispersed in a sample matrix comprising:

a) means for generating an uninterrupted probe beam of the said radiation which contains, alternating in time, at a predetermined alternating frequency, half-periods of two different and substantially monochromatic wavelengths $\lambda_2$ and $\lambda_2$ and at the two wavelengths, the extinction caused by the combined effects of absorption and scattering of the radiation in the matrix is equal, but the absorption produced by the analyte is different;

b) splitting means for splitting this probe beam into a sample beam and a reference beam and means for transmitting the sample beam into a sample of the sample matrix;

c) first detector means for detecting said sample beam after it has traversed the matrix, and for generating in response an AC sample signal and means to amplify and rectify this AC sample signal to produce a DC sample signal at the wavelength-alternating frequency;

d) means for optically controlling the intensity ratio of the $\lambda_1$ and $\lambda_2$ half-periods so that the signal from the test detector will be essentially zero when there is no analyte in the sample;

e) second detector means for detecting said reference beam and for generating in response an AC reference signal and means to amplify and rectify this AC reference signal to generate a DC reference signal; and f) intensity control means for maintaining constant the intensity ratio of the two different wavelength half-periods of the probe beam when analyte is present in the sample using the signal from the DC reference signal, and display means for displaying the DC sample signal.

* * * * *